United States Patent [19]

Goldner et al.

[11] Patent Number: 5,270,000

[45] Date of Patent: Dec. 14, 1993

[54] APPARATUS AND PROCESS FOR TREATING MEDICAL HAZARDOUS WASTES

[75] Inventors: Helmut Goldner, Neinburg; Reinhold Kamann, Wienhausen; Heinz Leinski, Wathlingen, all of Fed. Rep. of Germany

[73] Assignee: ABB Sanitec, Inc., Wayne, N.J.

[21] Appl. No.: 768,870

[22] PCT Filed: Apr. 16, 1990

[86] PCT No.: PCT/US90/02043

§ 371 Date: Oct. 31, 1991

§ 102(e) Date: Oct. 31, 1991

[87] PCT Pub. No.: WO90/12602

PCT Pub. Date: Nov. 1, 1990

[51] Int. Cl.⁵ .............. A61L 2/00; B01B 1/00; B01J 2/00

[52] U.S. Cl. .............. 422/21; 422/307; 422/308; 422/309; 34/1 R; 180/309

[58] Field of Search .............. 422/21, 307, 308, 309; 34/1 R; 219/10.55 R, 10.55 F; 222/181, 185; 180/309

[56] References Cited

U.S. PATENT DOCUMENTS

| | | | |
|---|---|---|---|
| 1,594,894 | 8/1926 | Masury | 180/309 |
| 3,295,982 | 1/1967 | Hickey et al. | 422/307 |
| 3,664,706 | 5/1972 | Chant | 180/309 |
| 3,831,288 | 8/1974 | Stribling et al. | 210/748 |
| 3,853,480 | 12/1974 | Kaelin | 422/233 |
| 4,351,644 | 9/1982 | Kriebitzsch et al. | 422/307 |
| 4,371,503 | 2/1983 | Aichelmann et al. | 422/307 |
| 4,546,226 | 10/1985 | Trembley et al. | 425/145 |
| 4,551,057 | 11/1985 | Naab | 414/420 |
| 4,608,261 | 8/1986 | MacKenzie | 426/242 |
| 4,832,700 | 5/1989 | Kaspar et al. | 422/143 |
| 4,999,471 | 3/1991 | Guarneri et al. | 219/10.55 M |

FOREIGN PATENT DOCUMENTS 271454 9/1989 Netherlands .............. 422/21

Primary Examiner—Robert J. Warden
Assistant Examiner—Krisanne M. Thornton
Attorney, Agent, or Firm—Chilton, Alix & Van Kirk

[57] ABSTRACT

The invention relates to an apparatus and a process for treating medical hazardous wastes to process them into waste similar to domestic refuse which can be removed or disposed of like normal domestic refuse or can be supplied for recycling after sorting. The infectious refuse is passed through a microwave chamber fitted with a plurality of microwave sources disposed next to each other and subjected to a disinfection therein. To achieve a safe and reliable treatment for decontaminating medical hazardous wastes in an economical and environmentally friendly manner, the apparatus has a two-stage construction of microwave chamber and temperature maintenance chamber. The microwave chamber has a dense microwave field distribution for heating the refuse to or above a selectable minimum temperature. Connected to the outlet of the microwave chamber is the temperature maintenance chamber which holds the refuse at at least the minimum temperature during a minimum residence time.

18 Claims, 7 Drawing Sheets

APPARATUS AND PROCESS FOR TREATING MEDICAL HAZARDOUS WASTES

The invention relates to an apparatus and a process for treating medical hazardous wastes.

A large quantity of potentially infectious refuse, such as, for example, non-returnable material, bandages, syringes and cannulas which have come into contact with infectious patients and of infectious refuse, such as, for example, wastes microbially contaminated with bacteria, viruses or spores is produced daily in hospitals, medical laboratories, doctors practices and other establishments of the health service. These medical hazardous wastes require special measures for preventing infection during storage and transportation.

A known waste disposal measure is therefore to collect this hazardous refuse in securely sealed non-returnable containers with subsequent incineration in special plants. The infection hazards for the medical personnel and the risks in transportation to the incineration plant by means of road vehicles are, however, great. In addition, the incineration costs for the hazardous refuse is many times the costs for domestic refuse.

Another known waste disposal measure is to disinfect infectious waste and consequently to process them to form wastes similar to domestic refuse which can be removed or eliminated like normal domestic refuse or can be supplied for recycling after sorting. For this purpose, German Offenlegungsschrift 3,317,300 discloses a container for receiving specific hospital waste which after filling and introducing a disinfectant can either be placed in a microwave chamber or is itself equipped with a microwave source, with the result that the hazardous refuse is disinfected by a chemothermal destruction of the microorganisms. This container makes possible only a batchwise treatment of the hazardous refuse on a small scale, while preparatory waste disposal steps, such as comminution of the hazardous waste, do not ensure adequate infection prevention. From the point of view of environmental hygiene and the toxicity of the active disinfectant substances, chemical processes of this type can also be used only to a limited extent.

German patent specification 3,505,570 reveals an apparatus for treating infectious refuse with the aid of microwaves in which disinfection of infectious refuse is carried out in a continuously operating waste disposal plant in order to keep the risk of infection due to the release of infectious germs, bacteria etc. as low as possible. This compact waste disposal plant comprises a sluice room, a spray apparatus disposed therein for moistening the refuse with water and optionally with an addition of disinfectant, a refuse comminutor and a microwave chamber. The microwave chamber is constructed as a through tube which is at least partially transparent to microwaves, along which several microwave sources disposed adjacently to each other are provided. By means of a conveying device, the comminuted and moistened refuse is moved through the microwave chamber, in which process the microwave radiation results in a considerable heating of the refuse. The residence time of the refuse in the microwave chamber is controlled via the temperature, it being essential to achieve a temperature of approx. 135° C. and above up to a maximum of 200° C., depending on the material. The residence time of the refuse in the microwave chamber is then a few minutes. For throughput times with acceptable economic cost, a waste disposal plant of this type has not led to absolutely reliable disinfection, and this made an increased use of disinfectant necessary.

The object of the invention is therefore to provide an apparatus and a process of the type mentioned which makes possible a safe and reliable treatment for the disposal of medical hazardous wastes in an economical and environmentally friendly manner.

This object is achieved in accordance with the characterizing part of claims 1 and 34.

As a result of this, an apparatus and a process for treating medical hazardous wastes are provided which make it possible to reduce the germ count by thermal inactivation. Rapidly heating the comminuted moist refuse in the microwave chamber and holding the refuse at at least one selectable minimum temperature for a minimum residence time make it possible to match the treatment to the initial germ count and the germ types present in order to bring about an at least partial denaturation of proteins and nucleic acids in the bacteria, fungi and viruses under the influence of the moist heat. This damage is irreversible and results in a safe elimination of the growth and reproduction functions. A controlled partial germ destruction or inactivation, and consequently elimination of pathogens which are contained in or on the refuse particles can thus be achieved by a purely thermal disinfection. Infectious refuse is rapidly decontaminated with a high efficiency, the higher thermal content of moist air being exploited.

At the same time, the apparatus may be a fixed installation or may be exploited in mobile form. In areas with hospitals and other health service establishments with low refuse output, the apparatus may be accommodated, as a motor vehicle fixture, in a container which is driven up to the waste collection points of the hospitals at regular intervals. The use of this decentralized waste disposal system disposes of the medical wastes in an environment-conserving and cheap manner. The transportation of infectious waste by road and the infection hazard resulting therefrom are avoided. Because non-returnable collecting containers are no longer necessary, the volume of waste is considerably reduced, with the result that the costs of waste disposal are also reduced.

In the microwave chamber, the moist or moistened granulated refuse material is heated directly by the microwaves, which achieves a rapid heating of the granulated material to the boiling point of water. The steam formation and steam flow associated increase the heating therewith by indirect heating. Especially in the case of a refuse-specific material with poor thermal conductivity such as, for example, plastics, this results in a substantially faster and more economical heating of the refuse load. To improve a uniform temperature distribution over the cross-section of a certain layer thickness, the conveying device may be constructed as a microwave field distributor in the form of a shaftless metal conveying screw. This conveying screw consequently produces not only a thorough mixing of the refuse to be heated, but also produces multiple reflections, with the result that the occasional differences in heating are smoothed out by direct and indirect heating. Microwave reflection from the walls of the microwave chamber can be achieved by constructing the same as a metallic U trough. Improved mixing can furthermore be achieved by an inclined installation of the microwave chamber and the falling back of the granulated material produced thereby. Finally, to avoid heat losses, the microwave chamber may be insulated thermally and possibly have a back-up heating system.

While the dense microwave field distribution is exploited to achieve rapid heating in a first stage of the treatment, a processing temperature or region is maintained in a second stage in order to completely eliminate the pathogenic germs. In order to maintain a minimum temperature, the temperature maintenance chamber is preferably encased by a heating device. The refuse can be forced to travel through the temperature maintenance chamber during the selectable processing time by means of a conveying device or under the action of gravity.

For the purpose of semi-automatic or fully automatic operation, the apparatus may incorporate a programmable central control unit which monitors and controls the three regions comprising loading and comminution, heating, and temperature maintenance and makes possible a particular matching of the operating mode to the type and quantity of the hazardous refuse to be disposed of.

Further developments of the invention are to be found in the description and the subclaims below.

The invention is explained in more detail below with reference to the exemplary embodiments shown in the accompanying diagrams.

BRIEF DESCRIPTION OF THE DRAWINGS

FIG. 1 shows a first exemplary embodiment of an apparatus for treating medical hazardous wastes in a container 1 which integrates a loading section, a treatment section and an unloading section to form a compact waste disposal plant.

Figure 1:
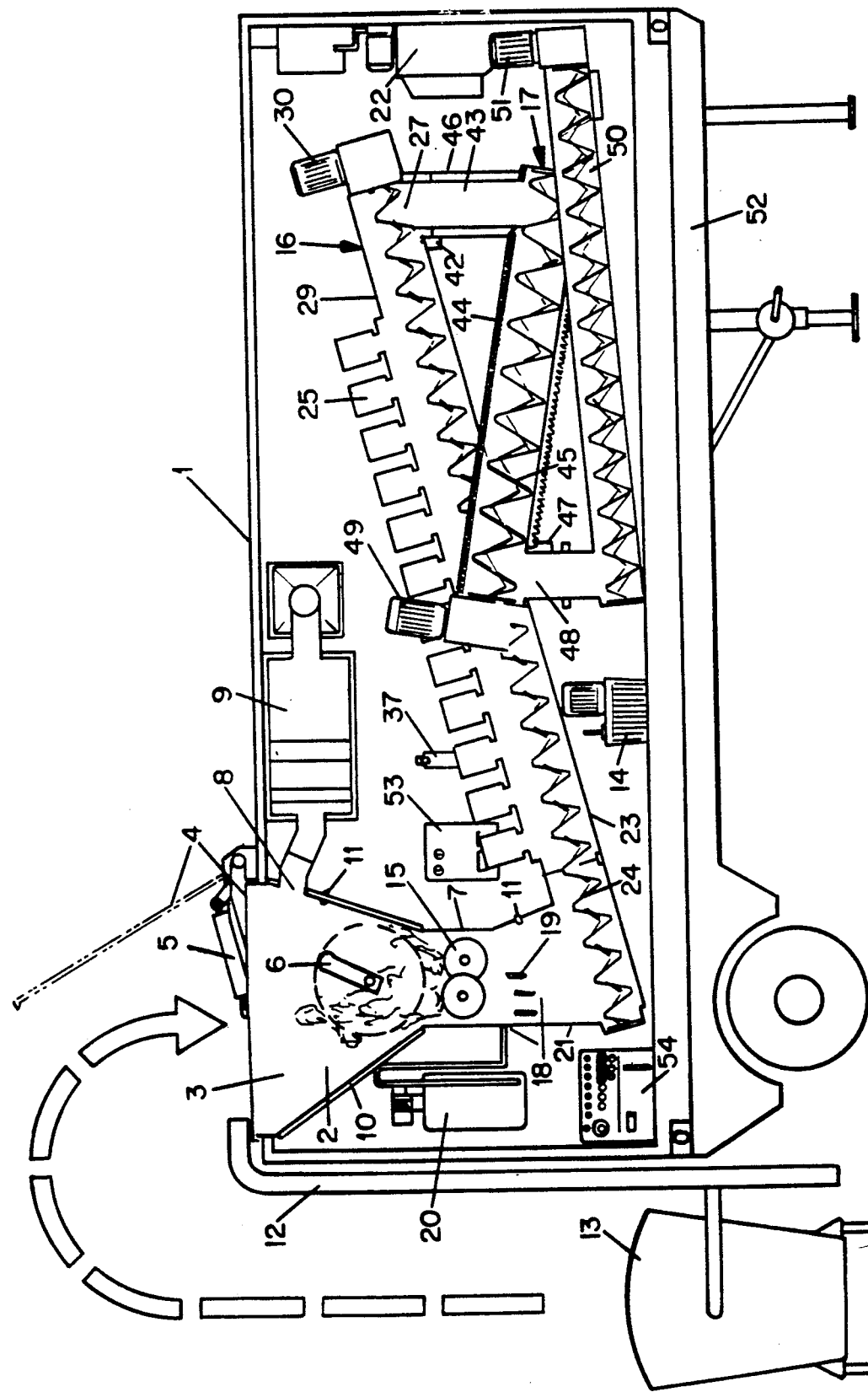
FIG. 1 shows a longitudinal section of a first exemplary embodiment of an apparatus for treating medical hazardous wastes, FIGS. 2a and 2b each show a half cross section of a microwave chamber of the apparatus according to FIG. 1.

To receive the articles of refuse 2 to be treated, the loading section first comprises a loading chamber 3 which is constructed as a funnel and can be sealed in a fluid-tight manner by means of a cover 4. The cover 4 is opened and closed by means of hydraulic cylinders 5 by means of which the cover 4 is mounted on the roof of the container 1. Disposed inside the loading chamber 3 is a pushing device which is constructed as a rotating blade 6 and which precomminutes the refuse load 2 and feeds it to a refuse comminutor 7. The rotating blade 6 is driven by a geared motor. One or more suction slots 8 of a suction system 9 are disposed in the side walls 10 of the loading chamber 3 and form a suction screen which sucks off any atmospheric germs drawn up by opening the cover 4. In general, with cover 4 opened, the suction slots 8 remain in operation in order to prevent any escape of germs from the loading chamber 3. Preferably the suction system 9 comprises a roughing filter and a high-performance suspended-material filter. The funnel with cover 4 and suction system 9 provide the loading chamber 3 with the function of a waste sluice. An injection connection 11 with associated valve is furthermore let into the side wall 10 in order that superheated steam can be introduced into the waste disposal plant for the purpose of decontamination during stoppage, at shift end and also for repair and maintenance operations.

In order that no germs deposit on the side walls 10 the latter can furthermore be superficially heated using a back-up heating system. The side walls 10 are heated to a temperature of over 100° C., preferably to temperatures between 105° C. and 140° C.

The articles of waste 2 can be loaded manually, or automatically by means of a lift-and-tip device 12 which picks up waste containers 13 and empties them into the loading chamber 3. For this purpose, the lift-and-tip device 12 may be disposed at the rearside of the container 1 and moves one or more refuse containers 13 in the direction of the arrow for the particular loading operation. The waste containers 13 are preferably 120 l to 1100 l containers. A hydraulic system 14 is provided for actuating the lift-and-tip device 12. A weighing device may be integrated into the lift-and-tip device 12 to determine the weight per waste container 13 and possibly record it electronically.

The refuse comminutor 7, which also forms part of the loading section, comprises a cutting mechanism having two contrary-running knife driving shafts 15 into which cutting bodies and drivers are inserted. The cutting bodies are so designed that a granulation of the waste material fed with the aid of the rotating blade 6 is achieved. The refuse is mixed at the same time. A controllable electric motor is provided for driving the refuse comminutor 7.

The treatment section comprises a microwave chamber 16 and a temperature maintenance chamber 17. The connection between the loading section and the treatment section is provided by a transfer funnel 18 which is detachably connected to the outlet of the refuse comminutor 7 and the inlet of the microwave chamber 16. The transfer funnel 18 is preferably flanged on. In the transfer funnel 18, use is made of a spraying head 19 which is connected to a water tank 20 fitted with a pump, but may also be connected to an external water main. The spraying device is used to spray in water in a controlled manner to achieve uniform moistening of the granulated material produced by the refuse comminutor 7 for the subsequent treatment. The water paths are preferably shut off and opened up by solenoid-operated valves. The spraying time and rest time may be varied by means of a timer as a function of the degree of moistness of the refuse load. The transfer funnel 18 is exploited as intermediate storage for the granulated material since the comminutor 7 generally provides more granulated material than the microwave chamber 16 can handle. A filling level sensor 21 for a minimum and maximum filling level is disposed in the region of the inlet and outlet to monitor the degree of filling of the transfer funnel 18. The electric motor of the refuse comminutor 7 is preferably controlled in a manner such that the filling level of the transfer funnel 18 always varies between the minimum and maximum filling level. The comminution operation can consequently be regulated by means of the filling level sensors 21. Finally, the transfer funnel may also incorporate a further injection connection 11 for introducing the superheated steam for decontaminating the emptied waste disposal plant. A steam generator 22 is fitted to supply these injection connections 11.

In the treatment section, the microwave chamber 16 is used to heat the comminuted and moist, possibly moistened, refuse in a continuous process with a selectable conveying speed and layer thickness of the comminuted refuse. The microwave chamber 16 comprises a duct-like trough 23 in which a conveying device 24 is disposed. Along the through housing 23, there is disposed a central microwave source with a waveguide system or a plurality of microwave sources 25 are disposed closely adjacent to each other. To couple in the microwave radiation, the trough 23 has inlet openings 26 or is composed of material transparent to microwaves in these regions. The microwave sources 25 may be disposed at a plurality of sides of the through housing 23. Under the action of the microwaves, the granulated material travelling through is heated up by internal heating and evaporated moisture. To trap the evaporating moisture, the through housing 23 and the microwave sources 25 attached thereto form a sealed treatment chamber. As conveying device 24, use may be made, for example, of a conveying screw, a conveying belt or a conveying ram. The conveying device 24 removes the comminuted refuse from the transfer funnel 18 and conveys it at an adjustable speed to the outlet 27 of the microwave chamber 16. The mixing of the conveyed granulated material may be improved by installing the microwave chamber 16 with an incline to achieve uniform irradiation and a good heat exchange. Since the microwave chamber is always only partially, preferably ⅔, filled, the granulated refuse material consequently always partially falls back again. The angle of inclination is preferably between 10° and 50°.

Figures 2A, 2B:
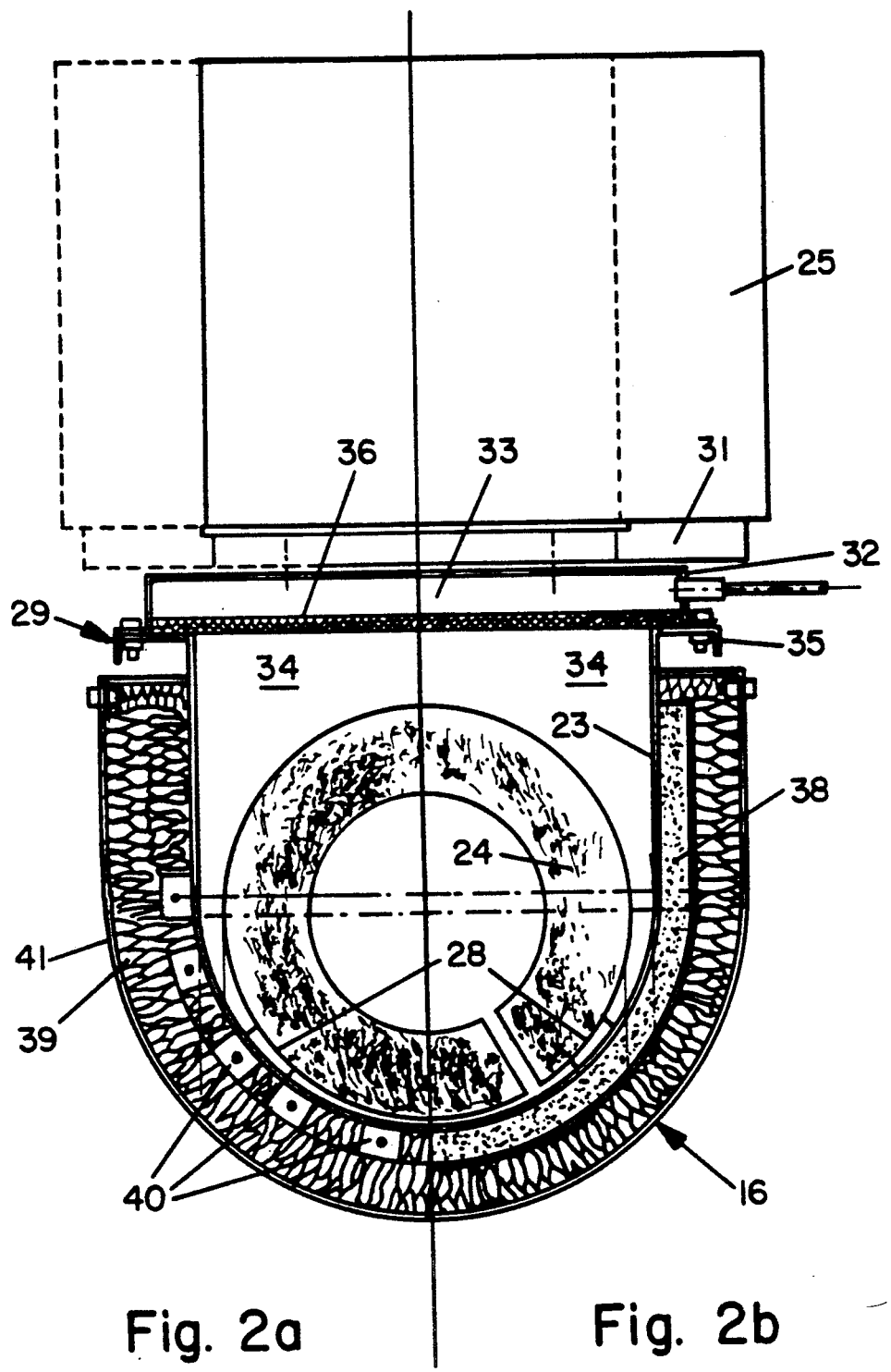

FIGS. 2a and 2b show the construction of the microwave chamber 16 in detail. The trough 23 is constructed as a U-shaped trough and the conveying device 24 comprises an open shaftless conveying helix which rotates in the U-shaped trough. The trough and conveying helix are composed of metal, preferably stainless steel, and additional wearing bars 28 of a softer material are provided on which the conveying helix runs. The trough 23 is closed in a fluid-tight manner by means of a trough cover 29 on which the microwave sources 25 are mounted. In the region of the microwave sources 25, the covering function of the trough cover 29 may also be taken over by the microwave sources 25 with guide system connected, as is further explained below. The trough dimensions depend on the required layer thickness in the microwave chamber 16, and the throughput quantity and throughput speed. Owing to the absence of a shaft, the conveying helix has a large free cross section which minimizes the risk of clogging and plug formation. The conveying helix furthermore acts as a three-dimensional field distributor for the microwaves coupled in, as a result of which the material to be treated is more satisfactorily reached by the microwave radiation. The conveying helix is driven by a motor 30 whose rotary speed can be controlled.

The heating in the microwave chamber 16 is achieved by two different heat injections while the material is passing through. A first heat injection is carried out by the microwave sources 25, 12 of which are disposed next to each other in this case but their number may, however, be between 1 and 20 depending on power level. The microwave energy produced by the individual microwave sources 25 is in each case coupled in via a waveguide 31 and deflectors 32, which form a resonance chamber 33, into the treatment chamber 34 of the microwave chamber 16. The deflectors 32 are attached to the trough 23 by means of detachable attachment devices 35. To produce a dense microwave field distribution, the resonance chambers 33 are disposed next to each other. To prevent refuse particles and moisture entering the waveguide 31 and the resonance chamber 33, the treatment chamber 34 is covered at the top by means of sheets 36 of a material which is transparent to microwaves such as, for example, polytetrafluoroethylene (PTFE). The switch-on time of the microwave sources 25 can be controlled. The electrical power may be supplied via a plug connection 37 (see FIG. 1). The switch-on times are selected in a manner such that the microwaves heat the granulated material to or above a selectable minimum temperature in order that the required thermal treatment, for example a disinfection, can be carried out. To guarantee heating at least to the minimum temperature, the conveying speed and filling levels are automatically adjusted.

A second heat injection is used to back up the heating produced by the microwaves. For this purpose, the trough 23 is surrounded by a heating device. According to FIG. 2a, the heating device comprises electrical heating coils 40 which are preferably disposed immediately next to the wall of the trough 23. According to FIG. 2b, the heating device comprises a double-walled partial jacket 38 for a heat transfer medium such as, for example, thermal oil or superheated steam, which partial jacket is also preferably disposed immediately next to the wall of the trough 23. A thermal insulation 39, which is screened on the outside by a covering 41, is adjacently installed in both designs. This second heat injection may comprise different heating circuits in order that a controlled continuous quantity of heat can be fed to the individual regions of the microwave chamber 16. The temperature reached by the granulated material is determined in the region of the inlet 43 of the temperature maintenance chamber 17 by means of a measuring sensor 42. To thermally disinfect a moist medium, the minimum temperature is above 95° C. and is preferably 98° C. to 102° C.

The outlet 27 of the microwave chamber 16 is connected to the inlet 43 of the temperature maintanance chamber 17. The temperature maintenance chamber 17 comprises a duct-like through housing 44 in which the temperature treatment of the granulated material takes place in a continuous process. The heated granulated material supplied by the conveying device 24 of the microwave chamber 16 is taken over by means of a conveying device 45 and passed through the temperature maintenance chamber 17 during a selectable minimum residence time. During this time, the granulated material is held at at least the minimum temperature. According to FIG. 1, the trough 44 is encased on the outside by a heating device 46 which is constructed, for example, as in the case of the microwave chamber 16. The heat introduced by the heating device 46 prevents the granulated material cooling down, with the result that the temperature produced in the microwave chamber 16 can be maintained. A temperature level may optionally be adjusted between inlet 43 and outlet 48 of the temperature maintenance chamber 17, in which case the inlet and outlet temperature must have at least a minimum temperature necessary for the treatment operation. To monitor the treatment operation, the inlet temperature is measured and documented by means of the measuring sensor 42 and the outlet temperature of the granulated material in the temperature maintenance chamber 17 by means of a measuring sensor 47.

The conveying device 45 comprises a conveying screw which, like the one in the microwave chamber 16, is of shaftless construction. The conveying screw 45 is driven by a motor 49 with controllable rotary speed. Its rotary speed is matched to the conveying helix 24 in a manner such that a certain compacting of the granulated material, which is initially loose for heating by microwaves, is brought about in the temperature maintenance chamber 17, as a result of which the heat conduction is improved in this treatment phase and the heat losses are reduced. Metals, preferably stainless steel, are envisaged as the material for the through 44 and the conveying device 45. However, plastics or ceramic materials may also be used. Since the treatment operation is complete at the outlet 48 of the temperature maintenance chamber 17, an adjoining unloading section may comprise only an ejection opening or, as shown in FIG. 1, it may have an unloading screw 50, driven by a motor 51, which can be swung laterally out of the container 1.

The container 1 shown in FIG. 1 can be a stationary installation or, according to FIG. 1, be disposed on a motor vehicle trailer 52 for mobile use. A space heating system 53 ensures an adequate ambient temperature.

Figure 3:
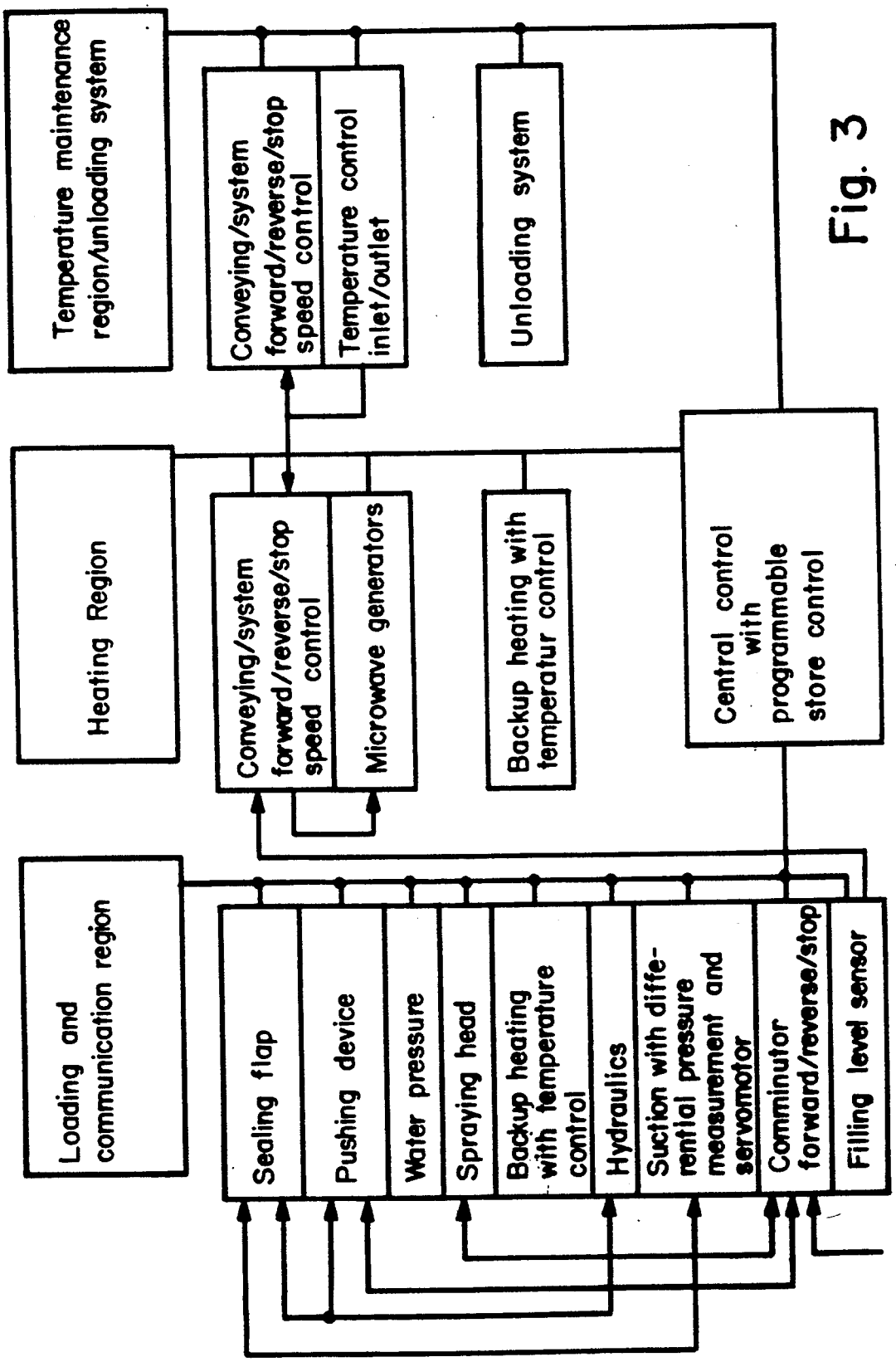
FIG. 3 shows a block diagram of functional units of the apparatus according to FIG. 1.

The waste disposal plant may be operated manually, or semiautomatically or fully automatically. All the essential controlled variables and monitoring functions are incorporated in a process-control computer 54. The center piece of the process-control computer 54 is a stored-program control system which contains an operating program for switch and sensor scanning, motor and source control, and monitoring and driving the indicators. The function units connected to the process-control computer 54 are shown in a block circuit diagram of FIG. 3 for the loading and comminution region, the heating region and the temperature maintenance region with unloading system. The controlled variables of the function units which affect each other are denoted by connecting lines with arrows. This measure ensures that the variables, critical for a thermal treatment, in particular a disinfection, of minimum temperature and maintenance duration are maintained and deviations are automatically corrected.

The mode of operation of the apparatus described above for treating medical hazardous wastes is described below for exemplary technical data relating to purely thermal disinfection of hazardous wastes.

To operate a plant with a processing capacity of 100 to 300 kg/h, the trough heating systems and the funnel heating systems are first switched on. Once the specified set temperature is reached, water and air pressure are available and the cover of the loading sluice is closed, the plant can be switched to automatic operation observing the safety requirements and loaded.

The lift-and-tip device 12, which also controls the opening of the cover 4, ejects wastes from the containers 13 to be emptied into the opened funnel 3. After the cover 4 has closed, the suction system 8 is switched off. The rotating blade 6 and the comminutor 7 are then set in operation. The rotating blade 6 shreds the articles of waste and feeds them in a controlled manner to the comminutor 7 which provides for granulation and mixing. The granulated material then drops into the transfer funnel 18 with automatic filling level monitoring and controlled moistening. The filling level monitoring regulates the comminution operation by switching off the comminutor 17 if the transfer funnel 18 is filled and stopping the further process sequence if the transfer funnel 18 is empty. If the lower filling level sensor 21 indicates the presence of granulated material, the conveying helixes of the microwave chamber 16 and the temperature maintenance chamber 17 and, with a time delay, the microwave sources 25 are automatically switched on. The thermal disinfection is now initiated. The granulated material is heated in the microwave chamber at a microwave frequency of 2,450 MHz approved here for industrial purposes. The granulated material is passed at a defined conveying speed through the microwave chamber 16 where a rapid direct production of heat is brought about in the material as a function of the dielectric properties. This effect is increased further by the water added which evaporates under the action of the microwaves. This application of vapor is maintained in the microwave chamber 16 since at the outlet side a natural seal is built up by the granulated material transferred to the temperature maintenance chamber 17. The granulated material temperature reached is subject to monitoring. If it drops below a minimum temperature, the conveying speed is reduced until the minimum temperature is reached again. In this process, the rotary speed of the conveying helix 24 is adjusted to the mean throughout level (kg/h) and the minimum temperature to be reached.

The final structural group for the disinfection is the temperature maintenance chamber 17 with its maintenance zone. In this maintenance zone, the granulated material is held at the minimum temperature, achieved by means of microwaves, of over 95° C. to eliminate the pathogenic germs. The minimum residence time depends on the number of germs, the germ type and the filling quantity. The maintenance time can be adjusted in a controlled manner by means of the speed of the conveying screw 45. The minimum temperature is demonstrated by documenting the automatically measured inlet and outlet temperature. Temperature losses are compensated for by the backup heating. If the transfer funnel 18 is empty, the microwaves sources 25 and, with a certain lag, the conveying devices 24, 45 are first switched off automatically. The treated granulated material is ejected for removal. After the completion of work, the plant is steam-disinfected.

A process according to the invention for continuously heat-treating particulate articles, in particular for disinfecting, sterilizing or preserving, comprises the following two steps. In a first step, the comminuted or already partly particulate articles are loosened up after carrying out moistening with an aqueous medium and passed through a microwave field while mixing the entire cross section of the conveyed layer thickness, and heated in this process to a minimum temperature with internal heating. In a second step, the articles so heated are at least slightly compacted and held at at least the minimum temperature during a minimum residence time. To maintain this minimum temperature with heat losses occurring, the articles can be heated indirectly during this holding phase so that any drop below the minimum temperature is avoided. This ensures, with as low a radiation of microwave energy as possible, the heating required for the heat treatment and, in addition, employed for the subsequent steps, which creates a high efficiency. In this process, the articles may be held, for example, at the minimum temperature until they are dried. If the use of disinfectants is additionally required for a treatment operation, spray injection of the same is possible during the first and/or second step.

Figure 4:
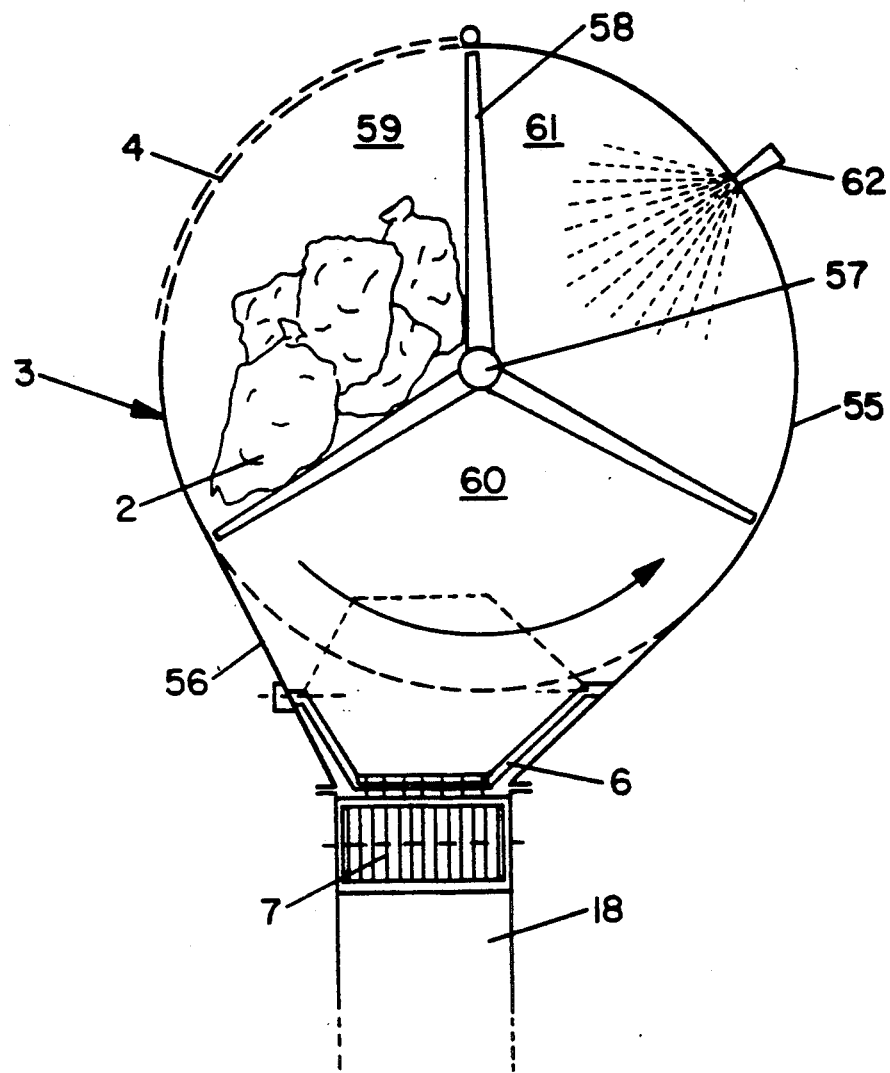
FIG. 4 shows a longitudinal section of another embodiment of the loading and comminution region.

FIG. 4 shows another embodiment of the loading and comminution region, in particular the loading chamber 3, which is constructed as a three-chamber sluice. The loading chamber has an essentially cylindrical hollow body 55 which is provided at the bottom with a funnel-type discharge section 56. Disposed centrally in the hollow body 55 is a sluice wheel 57 with three sluice paddles 58 each extending outwards at an angle of 120° in each case. The sluice paddles subdivide the hollow body 55 into three chambers which are separated from each other and which rotate anticlockwise in the direction of the arrow when the sluice wheel 57 turns. The sluice chambers pass through in sequence a filling station 59, a transfer station 60 and a disinfection station 61. The passage through the three stations 59, 60, 61 is described below for one chamber. If the sluice wheel 58 is in the position shown in FIG. 4, wastes 2 can be loaded into the chamber situated in the filling station after the cover 4 has been opened. Turning through 120° rotates this chamber with the wastes 2 received into the transfer station 60, where the rotating blade 6 operates and a transfer to the comminutor 7 takes place. The emptied chamber is then brought to the disinfection station 61 which is equipped with at least one spraying head 62 for introducing a disinfection mist and which can be extracted with a suction system 9 according to FIG. 1. The first chamber, freed of germs, is then transferred again to the filling station. The chambers roasted through 120° and 240° with respect to this chamber pass through said stations 59, 60, 61 with a displacement in time, as a result of which continuous loading with wastes 2 is possible. The region of the loading chamber opened for a loading is consequently always germ-free.

Figure 5:
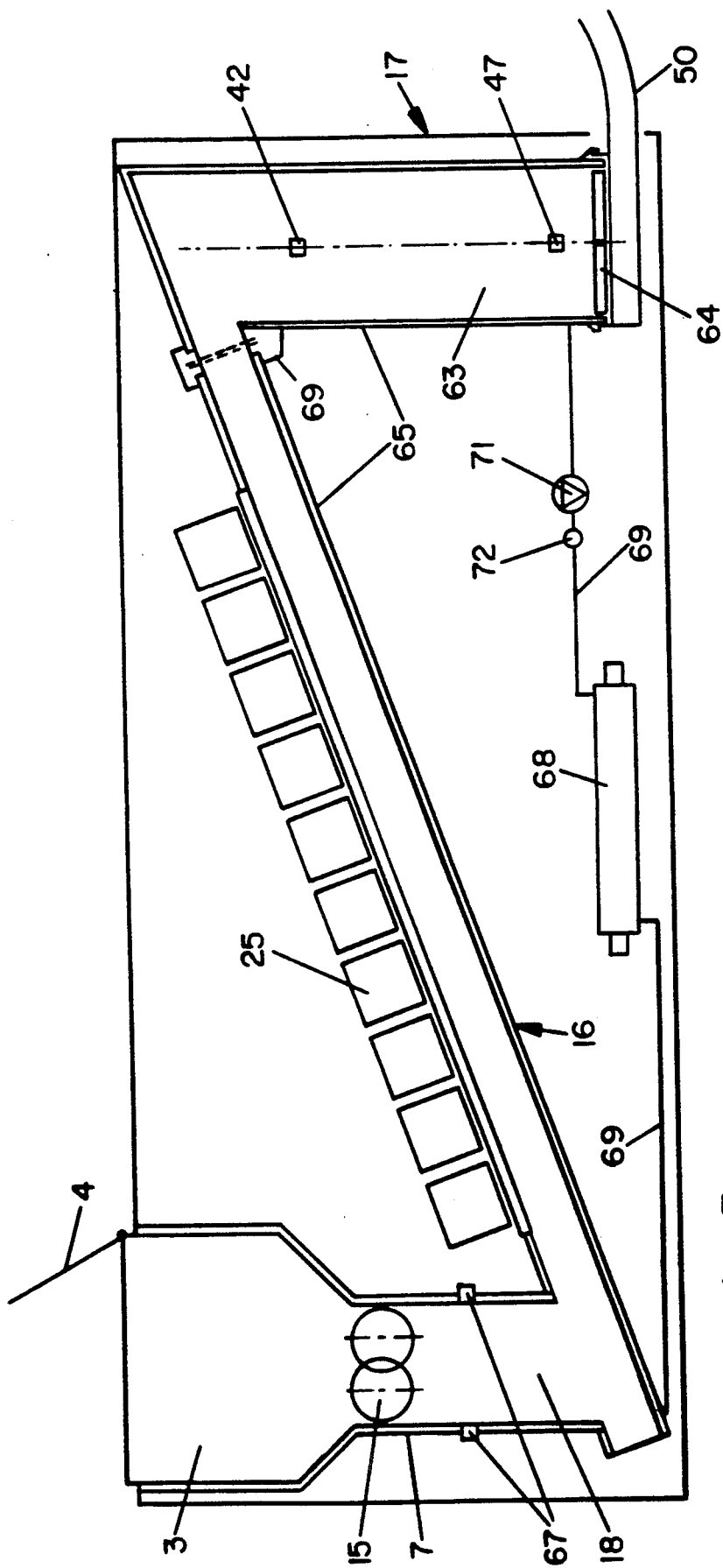
FIG. 5 shows a longitudinal section of a second exemplary embodiment of an apparatus for treating medical hazardous wastes.

FIG. 5 shows a second exemplary embodiment of the apparatus for treating medical wastes. The temperature maintenance chamber 17 is in this case constructed as a compact large-volume container 63. This container 63 is installed essentially vertically so that after the plant has been put into operation, the granulated material heated up in the microwave chamber 16 drops down under the action of gravity into the container 63 and fills the latter. In order to prevent material which has not yet been adequately thermally treated escaping during the first filling of the container 63, the container 63 is sealed at the bottom with a removable cover 64. The granulated material loaded into the container 63 remains in the latter for a minimum residence time at at least the minimum temperature. Depending on the required thermal treatment, e.g. disinfection, the minimum temperature and minimum residence time can be correspondingly adjusted and checked by means of the temperature measuring sensors 42, 47. For continuous operation, the cover 64 is removed after a first filling of the container 63. The granulated material transferred from the conveying device of the microwave chamber 16 to the temperature maintenance chamber causes the granulated material already loaded into the container 63 to travel through. The dimensions of the container 63 can be matched to the throughput quantity of the plant. The cross section of the unloading device 50 connected to the bottom of the container 63 is of smaller construction than the cross section of the conveying duct of the microwave chamber 16 so that more granulated material is constantly transferred from the microwave chamber 16 to the container 63 than can be delivered by the latter via the unloading device 50, as a result of which a compacting of the granulated material in the container 63 is achieved.

The second heat injection for the microwave chamber 16 and an indirect heating of the granulated material in the container 63 is carried out in the case of the plant according to FIG. 5 by means of a heat transfer medium. For this purpose, the microwave chamber 16 and the container 63 have chambered walls with a double jacket 65 through which the heat transfer medium, for example thermal oil, superheated steam, is pumped from a reservoir 68. The double jackets 65 of the microwave chamber 16 and of the container 63 are connected to each other to form a circuit for the heat transfer medium via pipelines 69 in which a pump 71 and at least one valve 72 are fitted for supply and control. The heating device of the loading chamber 3 can also be fed from this heat transfer circuit. The preheating of the granulated material thus achieved in the transfer funnel 18 is checked by means of temperature sensors 67. In other respects, the plant can be constructed as described in relation to FIGS. 1 to 4 and may also be equipped with an electrical heating system.

Figure 6:
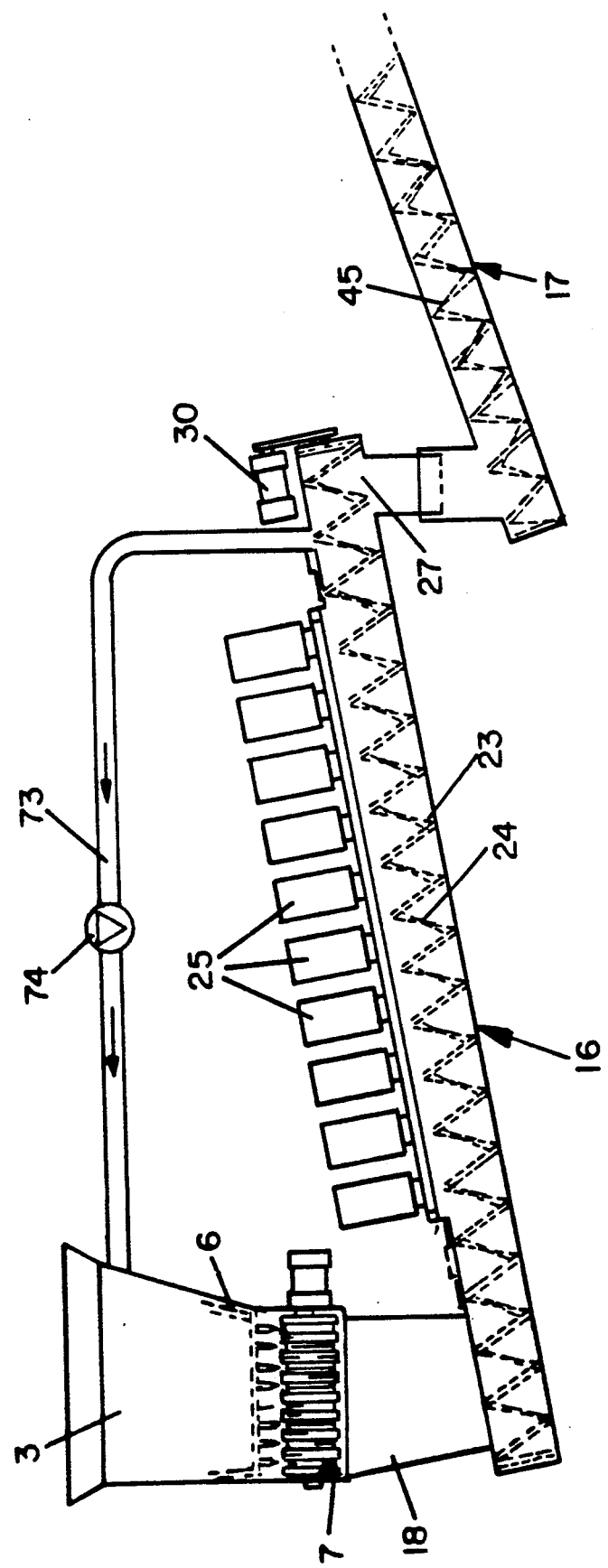
FIG. 6 shows a longitudinal section of a third exemplary embodiment of an apparatus for treating medical hazardous wastes.

FIG. 6 shows a third exemplary embodiment of an apparatus for treating medical hazardous wastes in which the heat produced in the microwave irradiation of the moistened waste can be at least partially recovered. For this purpose a circulating air pipeline 73 which can be shut off and which is led into the loading chamber 3 is connected in the region of the outlet 27 of the microwave chamber 16. Hot air can be sucked out of the housing duct 23 of the microwave chamber 16 by means of a pump 74 inserted in the circulating air pipeline 73 and fed to the funnel-type loading chamber 3. In other respects, this plant does not differ from that described in FIG. 1.

Figure 7:
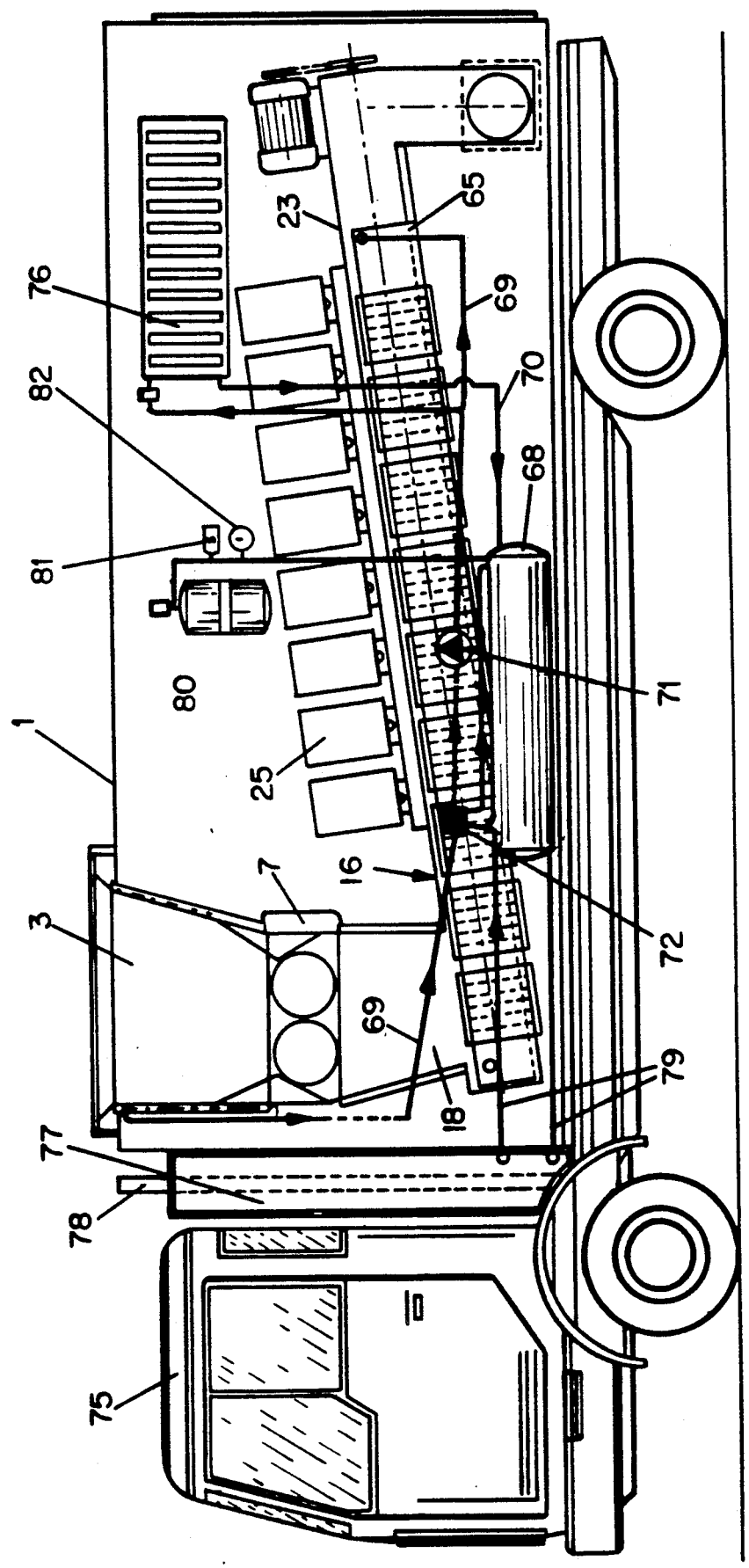
FIG. 7 shows a longitudinal section of a mobile embodiment of an apparatus for treating medical hazardous wastes.

FIG. 7 shows a mobile embodiment of an apparatus for treating medical wastes. As described in relation to FIG. 1, this plant comprises a loading section with loading chamber 3, comminutor 7 and transfer funnel 18, a treatment section with microwave chamber 16 and also a temperature maintenance chamber and an unloading section, said operating units being accommodated in a container 1 which forms the superstructure of a motor vehicle 75. To simplify the graphical representation, the temperature maintenance chamber and the unloading section have been omitted. The plant is furthermore equipped with a heating device, described in relation to FIG. 5, by means of circulation of heat transfer oil. In this case, heat transfer oil is envisaged as heat transfer medium. Pipelines 69 with pump 71 inserted and valve 72 connect the reservoir 68 to the double-walled jackets 65 of the housing duct 23 of the microwave chamber 16 and of the loading chamber 3. A radiator 76 of the space heating system 53 (see FIG. 1) is fed via pipelines 70. An exhaust gas heat exchanger 77 which is disposed around the exhaust 78 of the motor vehicle 75 is provided to heat up the heat transfer oil stored in the reservoir 68. The reservoir 68 is connected to the exhaust gas heat exchanger 77 via pipelines 79 to heat up the heat transfer medium. To monitor and safeguard the heating of the heat transfer oil, an expansion vessel 80, a safety valve 81 and a pressure gauge 82 are connected to the reservoir 68. The heat produced in the internal combustion engine of the motor vehicle can thus be employed for the thermal treatment operation on the medical hazardous refuse in a manner such that the plant is heated up during the drive to the points of use without additional energy costs and preheating times and dwell times of the plant are minimized.

We claim:

1. An apparatus for treating moist infectious refuse with microwaves to heat refuse to at least a minimum temperature for disinfection, said apparatus comprising an outwardly sealable enclosure having a loading section and a treatment section, said loading section constructed and arranged to receive refuse and deliver refuse to said treatment section in a moist condition wherein said treatment section comprises:

a. a microwave chamber having an inlet and an output end and incorporating a microwave source and a conveying device constructed and arranged to move refuse from said inlet end to said output end past said microwave source for heating refuse to at least said minimum temperature; and b. a temperature maintenance chamber having an inlet and an outlet end, said inlet end connected to said output end of said microwave chamber, said temperature maintenance chamber incorporating a conveying device constructed and arranged to move refuse from said inlet end of said temperature maintenance chamber to said outlet end of said temperature maintenance chamber and heating means for maintaining the refuse at said minimum temperature during movement through said temperature maintenance chamber.

2. The apparatus as claimed in claim 1 wherein said loading section includes a comminutor constructed and arranged to granulate refuse.

3. The apparatus as claimed in claim 1 wherein said heating means in said temperature maintenance chamber for maintaining the refuse at said minimum temperature includes a heating device for indirectly heating the refuse.

4. The apparatus as claimed in claim 3 and further including temperature sensors disposed at said inlet and outlet ends of said temperature maintenance chamber constructed and arranged to control said heating device.

5. The apparatus as claimed in claim 1 wherein said temperature maintenance chamber is formed by a housing duct and wherein said temperature maintenance chamber conveying device comprises a shaftless conveying screw in said housing duct.

6. The apparatus as claimed in claim 5 wherein said temperature maintenance chamber is at an angle of inclination rising from said inlet end to said outlet end.

7. The apparatus as claimed in claim 1 wherein said temperature maintenance chamber comprises a storage container, said storage container having an outlet opening at the bottom thereof for discharging refuse.

8. The apparatus as claimed in claim 7 and further including an unloading device disposed below said outlet of said storage container of said temperature maintenance chamber constructed and arranged to convey refuse away from said outlet opening is said storage container.

9. The apparatus as claimed in claim 8 wherein said microwave chamber is formed by a housing duct and wherein said conveying device is said microwave chamber comprises a helix screw conveyor.

10. The apparatus as claimed in claim 9 wherein said housing duct of said microwave chamber and said unloading device each have a cross sectional area through which refuse passes and wherein said cross sectional area of said housing duct of said microwave chamber is greater than the cross sectional area of said unloading device in order to at least partially compact refuse in said temperature maintenance chamber.

11. The apparatus as claimed in claim 1 wherein said conveying device in said microwave chamber comprises a shaftless stainless steel conveying screw.

12. The apparatus as claimed in claim 1 wherein said microwave chamber comprises a U-shaped trough and a trough cover mounted thereon and wherein said microwave source is attached to said trough cover.

13. The apparatus as claimed in claim 12 wherein said conveying device in said microwave chamber comprises a shaftless helix conveying screw and wherein said trough is composed of stainless steel and further includes wear bars constructed and arranged to support said shaftless conveying helix screw.

14. The apparatus as claimed in claim 12 wherein said trough is separated from said microwave source by means of a sheet of polytetrafluoroethylene in a fluid-tight manner.

15. The apparatus as claimed in claim 12 wherein said trough further includes a heating device for heating said trough.

16. The apparatus as claimed in claim 1 wherein said microwave chamber is formed by a housing duct and wherein said microwave source comprises a plurality of separate microwave sources and wave guides disposed next to each other including resonant cavities attaching said plurality of microwave sources to said housing duct.

17. The apparatus as claimed in claim 1 and further including a spraying device disposed in said loading section for moistening refuse.

18. A process for continuously heat-treating particulate articles for disinfecting and sterilizing comprising the steps of moistening said articles, passing said articles through a microwave field, mixing said articles during passage through said microwave field, whereby said articles are heated to a disinfecting and sterilizing temperature, passing said articles from said microwave field to a temperature maintenance zone in which said temperature is maintained and wherein said articles are at least partially compacted and discharging said articles from said temperature maintenance zone.

* * * * *